(12) United States Patent
Bille

(10) Patent No.: US 6,220,707 B1
(45) Date of Patent: Apr. 24, 2001

(54) METHOD FOR PROGRAMMING AN ACTIVE MIRROR TO MIMIC A WAVEFRONT

(75) Inventor: Josef Bille, Heidelberg (DE)

(73) Assignee: 20/10 Perfect Vision Optische Geraete GmbH, Heidelberg (DE)

( * ) Notice: Subject to any disclaimer, the term of this patent is extended or adjusted under 35 U.S.C. 154(b) by 0 days.

(21) Appl. No.: 09/512,440

(22) Filed: Feb. 25, 2000

(51) Int. Cl.$^7$ ........................................................ A61B 3/10
(52) U.S. Cl. ............................................................ 351/212
(58) Field of Search .................................... 351/205, 206, 351/211, 212, 214, 221; 623/4, 5; 356/512, 513, 514, 515, 121

(56) References Cited

U.S. PATENT DOCUMENTS

| | | |
|---|---|---|
| 4,732,473 | 3/1988 | Bille et al. . |
| 5,062,702 | 11/1991 | Bille . |
| 5,777,719 | 7/1998 | Williams . |
| 5,949,521 | 9/1999 | Williams . |
| 6,002,484 | * 12/1999 | Rozema et al. .................... 356/354 |
| 6,007,204 | * 12/1999 | Fahrenkrug et al. ............... 351/221 |
| 6,050,687 | * 4/2000 | Bille et al. ......................... 351/212 |
| 6,086,204 | * 7/2000 | Magnante ........................... 351/205 |
| 6,155,684 | * 12/2000 | Bille et al. ......................... 351/212 |

OTHER PUBLICATIONS

Cubalchini, Modal Wave–Front Estimation from Phase Derivative Measurements, pp. ?, Hughes Aircraft Co., Nov. 6, 1978.

Wang, Wave–Front Interpretation with Zernike Polynomials, pp. 1510–1518, Applied Optics, vol. 9, No. 9, May 1, 1980.

Southwell, Wave–Front Estimation from Wave–Front Slope Measurements, pp. 998–1005, J. Opt. Soc. Am., vol. 70, No. 8, Aug. 1980.*

Walsh et al., Objective Technique for the Determination of Monochromatic Aberrations of the Human Eye, pp. 987–992, J. Opt. Soc. Am., vol. 1, No. 9, Sep. 1984.*

Freischlad et al., Modal Estimation of a Wave Front From Difference Measurements Using the Discrete Fourier Transform, J. Opt. Soc. Am, vol. 3, No. 11, Nov. 1986.*

Klyce et al., Imaging, Reconstruction, and Display of Corneal Topography, pp. 409–416, SPIE, vol. 1161, New Methods in Microscopy and Low Light Imaging (1989).*

Bille et al., Imaging of the Retina by Scanning Laser Topography, pp. 417–425, SPIE, vol. 1161, New Methods in Microscopy and Low Light Imaging (1989).*

Baker, Holographic Contour Analysis of the Cornea, pp. 426–437, SPIE, vol. 1161, New Methods in Microscopy and Low Light Imaging (1989).*

Liang et al., Objective Measurement of Wave Aberrations of the Human Eye with the Use of a Hartmann–Shack Wave–Front Sensor, pp. 1949–1957, J. Opt. Soc. Am., vol. 11, No. 7, Jul. 1994.*

* cited by examiner

Primary Examiner—George Manuel
(74) Attorney, Agent, or Firm—Nydegger & Associates

(57) ABSTRACT

A method for programming an active mirror to transform between a distorted wavefront and a plane wavefront requires independently moving each facet of the active mirror along a respective path. The method includes positioning the facets to respectively reflect a light beam in the wavefront, and establishing a base datum for the facets that corresponds to a plane wavefront. The individual phase shift deviation from a plane wavefront is measured for each light beam, and each respective facet is then moved to minimize the individual deviation. The method also requires that groups of facets act together in regions, such that each facet in a particular region will have a total phase shift that includes the individual deviation, the so-called modulo $2\pi$ phase shift, plus a same modular phase shift. The modular phase shift for each facet in a region is measured from a plane wavefront and is equal to $n2\pi$. Accordingly, moving facets to compensate for individual deviations is accomplished by effectively subtracting the modular from the total phase shift.

20 Claims, 2 Drawing Sheets

METHOD FOR PROGRAMMING AN ACTIVE MIRROR TO MIMIC A WAVEFRONT

FIELD OF THE INVENTION

The present invention pertains generally to diagnostic equipment which is useful for analyzing refractive properties of the eye. More particularly, the present invention pertains to equipment and methods for using this equipment which are capable of modeling a distorted wavefront of light that is characteristic of the refractive properties of an eye. The present invention is particularly, but not exclusively, useful as a method incorporating wavefront analysis for programming an active mirror so that the active mirror will mimic a particular wavefront of light.

BACKGROUND OF THE INVENTION

Wavefront analysis is based on the proposition that light has a characteristic wavelength, and that phase differences in wavelength between contiguous individual light beams are descriptive of the wavefront. In order to better understand this proposition, it is helpful to also understand the meanings of "wavefront" and "phase" in the context of light. By definition, wavelength is the distance between two similar and successive points on a harmonic (sinusoidal) wave, e.g. the distance between successive maxima or minima. Accordingly, in one wavelength, the waveform will go through one complete cycle from maxima to maxima, or minima to minima. Further, by definition, phase is the fraction of a cycle of a periodic waveform which has been completed at a specific reference time. Typically, the phase of a waveform is determined relative to the start of a cycle of another waveform of the same frequency. Further, phase can be expressed either as an angle, with one cycle corresponding to $2\pi$ radians (or 360°), or as a fraction of a wavelength ($\lambda$). For example, the same phase shift can be expressed either as a 90° phase shift, or as a $\lambda/4$ phase shift.

A wavefront of light can be thought of as a plurality of individual light beams which are all contiguous with each other. In accordance with the definitions given above, a plane wavefront of monochromatic light occurs when all of the light is in phase as it is incident on, or passes through, a plane that is oriented perpendicular to the path of the light. Thus, for a plane wavefront, the light in the wavefront can be thought of as including a plurality of contiguous individual light beams in which the light in any one light beam is in phase with the light in all of the other light beams. On the other hand, when light in one or more of these contiguous individual light beams is out of phase with the light in other light beams, i.e. there are phase deviations in the light, the result is a distorted wavefront. These phase deviations, however, can be measured and, thus, can be used to describe or define the wavefront. For example, methods for measuring phase deviations have been disclosed in conjunction with devices like the well known Hartmann-Shack sensor and in publications such as U.S. Pat. No. 5,062,702 which issued to Bille for an invention entitled "Device for Mapping Corneal Topography."

Insofar as an eye is concerned, it is known that a wavefront analysis can be used to determine the refractive properties of the eye. Also, by comparing the refractive properties of a particular eye to those of a "normal" eye, a wavefront analysis can be used to determine what corrective actions, if any, are appropriate. For these purposes, the "normal" eye is known to have a pupil that has an approximately six millimeter diameter, when dilated. Also, the "normal" eye is known to accommodate a maximum phase shift gradient of approximately one wavelength per millimeter ($1\lambda$/mm). Stated differently, a "normal" eye can effectively accommodate a phase change equal to one wavelength over a distance of one millimeter. For wavefront analysis, this one millimeter distance is taken in a direction that is perpendicular to the path of the contiguous individual light beams in the wavefront of light that is incident on the eye.

A widely used criteria for rating the quality of an optical system, either mechanical or anatomical, is the so-called Strehl ratio. Mathematically, the Strehl ratio, "S", can be expressed as $S=I/I_o$, where "I" is the maximum intensity of the real system being evaluated and, "$I_o$" is the maximum intensity of an ideal optical system (with the same aperture diameter and F/number). The Strehl ratio may be expressed either as a ratio or as a percentage. For an ideal optical system, the Strehl ratio is 1 or 100%. For a very good optical system the Strehl ratio is more than 0.9 or 90%, and for a diffraction limited system, the Strehl ratio should be greater than 0.8 or 80%. The Strehl ratio for a "normal" eye is 0.9 (S=90%) over a pupil with a diameter of approximately three millimeters (3 mm), under daylight illumination conditions.

With the above in mind, the optical capabilities of an eye can be described in terms of phase shift, phase shift gradient and the Strehl ratio. Specifically, it is known that the "normal" eye is able to accommodate an r.m.s. error in phase deviations of about $\lambda/14$ with a 3 mm pupil without any appreciable diminution in visual acuity. Insofar as phase shift gradient is concerned, as implied above, a gradient of $1\lambda$/mm is considered "normal" beyond the 3 mm pupil and corresponds to a Strehl ratio of approximately S=0.1 over a pupil of approximately 6 mm in diameter under twilight illumination conditions. Further, it is known that the steepest gradient which can be effectively accommodated by an eye is approximately $5\lambda$/mm.

Accordingly, in light of the above it is an object of the present invention to provide a method and device for programming an active mirror which will transform a distorted wavefront into a plane wavefront, and vice versa, while effectively compensating for as much as a $5\lambda$/mm phase shift gradient. Another object of the present invention is to provide a method and device for programming an active mirror which will transform a distorted wavefront into a plane wavefront, and vice versa, while accounting for modular $n2\pi$ (or $n\lambda$) phase shifts. Still another object of the present invention is to provide a method and device for programming an active mirror which is simple to use, relatively easy to manufacture and comparatively cost effective.

SUMMARY OF THE PREFERRED EMBODIMENTS

A method and device in accordance with the present invention includes an active mirror that includes an array of approximately forty thousand individual facets. Each facet in the active mirror is independently moveable along a respective substantially parallel path through a distance of approximately four tenths of a micron. Due to the fact that one wavelength of visible light ($1\lambda$) is approximately eight tenths of a micron, the individual and separate movement of each facet is able to compensate for phase shifts of about one full wavelength.

For the present invention, each facet in the active mirror is substantially square and is approximately forty microns by forty microns. Thus, as measured in a direction along side-by-side facets, there will be twenty-five such facets within each millimeter of length on the surface of the active mirror. This means that, from facet to facet there will be only a λ/25 phase shift error, at most. Importantly, this λ/25 phase shift error compares very favorably with the λ/14 r.m.s. error in wavefront phase shift which is accommodated by the normal eye and which corresponds to an acceptable diffraction limited performance for an eye. Further, it should be noted that the forty thousand facets in the array of the active mirror can be arranged in rows and columns that will each include two hundred facets. The result, using forty-micron square facets, is an eight millimeter by eight millimeter active mirror which can effectively accommodate all of the light that will pass through the six to seven millimeter diameter pupils of the human eye.

In operation, the individual facets of the active mirror are positioned so that each facet will respectively reflect a single light beam. Collectively, a plurality of these contiguous light beams make up a wavefront; which may or may not be distorted. Initially a base datum is established for all of the facets in the active mirror such that the base datum corresponds to a plane (undistorted) wavefront. Stated differently, with all facets at the base datum, the active mirror is configured substantially as a plane ordinary mirror.

For the present invention, a total deviation in phase shift is measured for each of the contiguous light beams in the wavefront. These phase shifts are measured relative to the phase of corresponding individual light beams in a plane wavefront, and are preferably made using a sensor of a type well known in the art, such as a Hartmann-Shack sensor. As so measured, the total phase shift deviation of a particular light beam will include two components. One is a modular "$n2\pi$" phase shift, and the other is an individual phase shift, i.e. the modulo $2\pi$ phase shift. Specifically, the modular phase shift is equivalent to a shift of whole wavelengths ($n\lambda$ or $n2\pi$), where "n" is an integer. On the other hand, the individual phase shift, the so-called modulo $2\pi$ phase shift, is measured beyond the modular "$n2\pi$" phase shift, is in addition to the modular phase shift, and will, itself, always be less than $2\pi$. Mathematically, this relationship is expressed as $n2\pi+\phi$; where $n2\pi$ is the modular component and $\phi$ is the modulo component. Accordingly, when $n2\pi+\phi$ is divided by $2\pi$, the result is "n" plus $\phi$ as a remainder.

Once the total phase shift has been determined for each of the individual contiguous light beams that make up the distorted wavefront, the active mirror is divided into regions. Specifically, one region is identified with an integer "n" wherein all of the individual light beams incident on facets in the "n" region have a same modular phase shift. As indicated above, this modular phase shift is equal to $n2\pi$. Next, boundary facets in the region are detected such that all of the boundary facets have an $(n+1)2\pi$ modular phase shift, with a zero individual phase shift deviation. An "n+1" region is then identified that is adjacent the boundary facets, but outside of the "n" region. All of the light beams incident on facets in this "n+1" region will have a respective modular phase shift that is equal to $(n+1)2\pi$. Similarly, other boundary facets may be detected which have an $(n-1)2\pi$ modular phase shift, with a zero individual phase shift deviation. If so, an "n-1" region is identified which is adjacent these boundary facets and which is outside the "n" region. Accordingly, all of the light beams incident on facets in the "n-1" region have a respective modular phase shift that is equal to $(n-1)2\pi$. In a like manner "n+2" and "n+3" regions etc., as well as "n-1" and "n-2 regions etc. can be identified.

The particular modular phase shift for each region is compensated for by subtracting $n2\pi$, $(n+1)2\pi$, or $(n-1)2\pi$, etc. as appropriate, from the total phase shift of individual light beams within the region. In this manner, the individual phase shift deviations for each individual light beam in the distorted wavefront is determined. Recall, these individual phase shifts will be less than $2\pi$ or, stated differently, less than one wavelength of visible light ($1\lambda$). Also, recall that one wavelength of visible light ($1\lambda$) is approximately eight tenths of a micron and that each facet in the active mirror is moveable through a distance of approximately four tenths of a micron. Thus, each facet in the active mirror can be moved from the base datum, and through a distance on its respective path, to minimize the individual phase shift deviation of the light beam that is incident on the particular facet. Collectively, when this compensation is made for all facets, the active mirror is able to effectively transform the plurality of contiguous light beams between a distorted wavefront and a plane wavefront.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
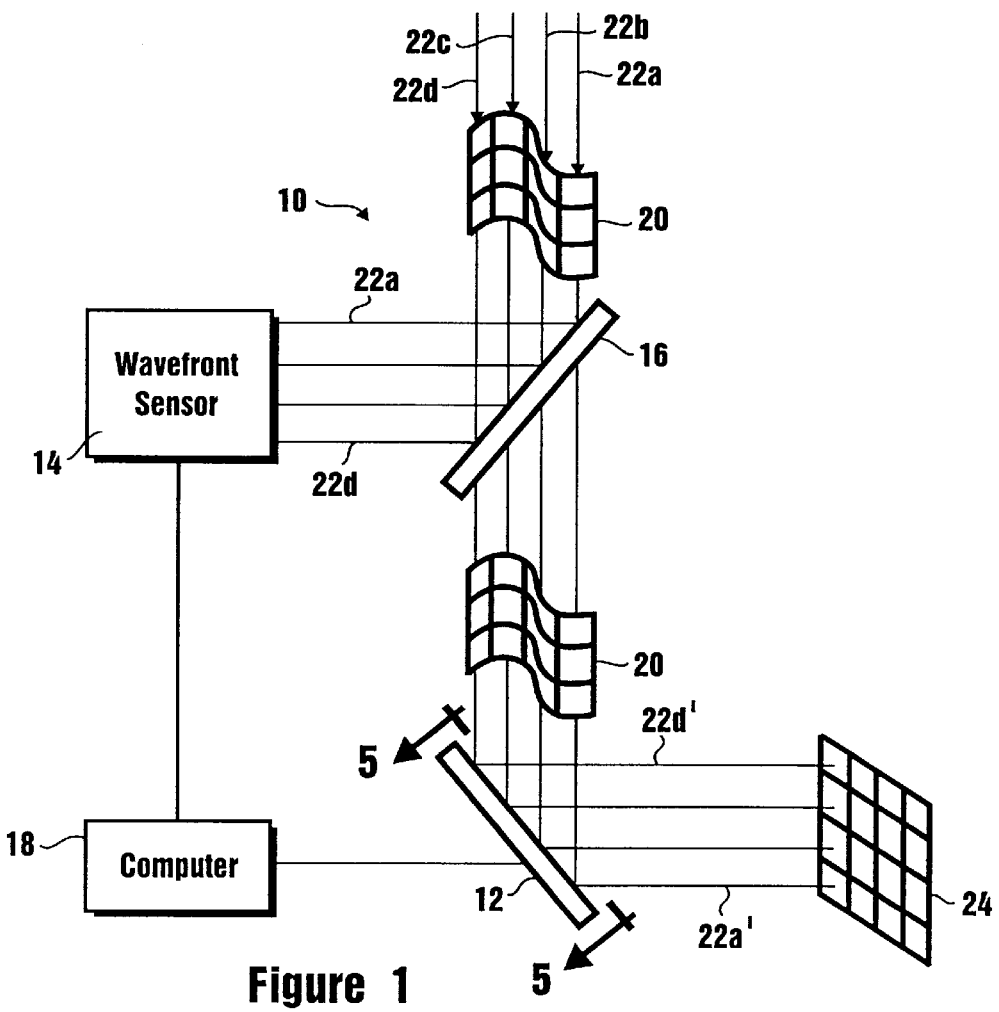
FIG. 1 is a schematic representation of a system for practicing the methods of the present invention.

Referring initially to FIG. 1, a system for practicing the methods of the present invention is shown and is generally designated 10. As shown, the system 10 basically includes an active mirror 12, a wavefront sensor 14, a beam splitter 16 and a computer 18. For purposes of the present invention, the wavefront sensor 14 can be of a type well known in the pertinent art, such as a Hartmann-Shack sensor. Likewise, the beam splitter 16 and the computer 18 can also be of types well known in the pertinent art. The active mirror 12, however, must be selected to have certain characteristics that will become more apparent in light of the disclosure presented herein.

In overview, the function of system 10 is to program the active mirror 12. Specifically, this is done to transform a distorted wavefront 20, which can be described by the phase differences between contiguous individual light beams 22, into a plane wavefront 24 wherein all of the contiguous individual light beams 22 are in phase with each other. For the discussion here, the individual contiguous light beams 22a, 22b, 22c and 22d are considered exemplary. At this point it is also helpful to appreciate that system 10 is also useful for transforming a plane wavefront 24 into a predetermined distorted wavefront 20. For either transformation, the notions of phase differences and phase shifts for the individual light beams 22 are important and will perhaps be best appreciated with reference to FIG. 2A and FIG. 2B.

Figure 2A:
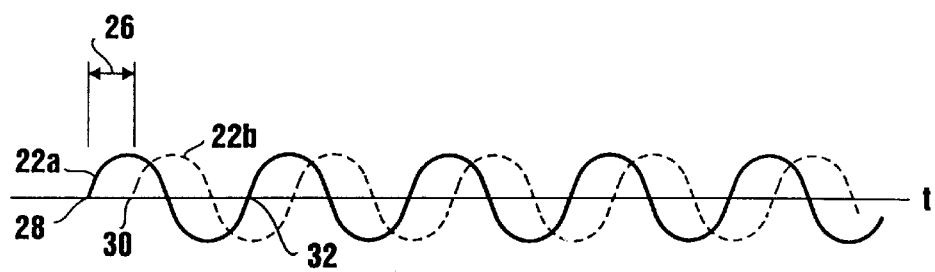
FIG. 2A is a sinusoidal illustration of a phase shift of less than $2\pi$ between a light beam in a distorted wavefront and an idealized light beam of a plane wavefront.

In FIG. 2A, the sinusoidal characteristic of the light beam 22a is shown as a function of time. Also shown FIG. 2A is the sinusoidal characteristic of the light beam 22b. If the light beams 22a and 22b were in phase with each other, which they are not in FIG. 2A, the light beam 22b would be shown superposed on top of the light beam 2a. As shown, however, the light beams 2a and 2b are out-of-phase relative to each other, and this difference in phase is shown as a phase shift 26. Conceptually, the phase shift 26 can be thought of as either a difference in time or a difference in distance traveled. For instance, at the specific point in time 28, the light beam 22a will be at a certain position in free space. Due to the phase shift 26, however, the light beam 22b will not be at this same position until the subsequent point in time 30. For the situation shown in FIG. 2A, and when considering that the light beam 22a will go through a complete period, or cycle, of 360° ($2\pi$ radians) as it travels from the point in time 28 to a point in time 32, it will be appreciated that the magnitude of the phase shift 26 between light beam 22a and light beam 22b is less than $2\pi$.

Figure 2B:
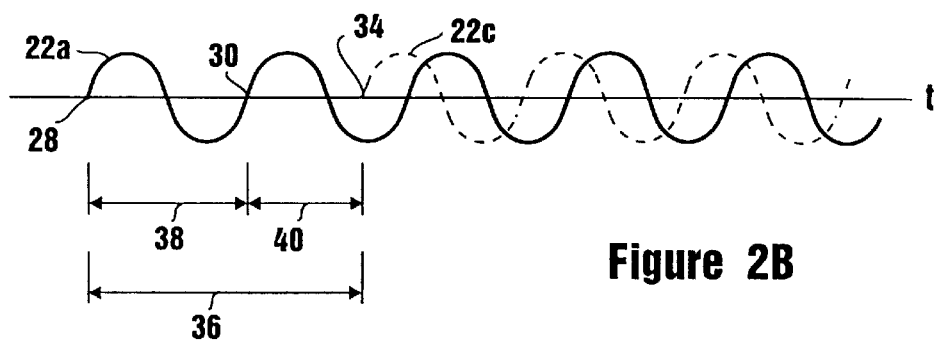
FIG. 2B is a sinusoidal illustration of a phase shift of more than $2\pi$ between a light beam in a distorted wavefront and an idealized light beam of a plane wavefront.

Now consider the relationship between the light beams 22a and 22c as depicted in FIG. 2B. For the particular condition shown in FIG. 2B, it is seen that the point in time 28 for light beam 22a corresponds to the point in time 34 for the light beam 22c. Thus, the total phase shift 36 which exists between the light beam 22a and the light beam 22c is more than $2\pi$. As contemplated for the present invention, the total phase shift 36 actually includes a modular phase shift 38 which is equal to $2\pi$, and an individual phase shift 40 which is less than $2\pi$. Using this notation, the total phase shift 36 between any two light beams 22 can be expressed as the sum of a modular phase shift 38 which is equal to $n2\pi$, where "n" is an integer, and an individual phase shift 40, the so-called modulo $2\pi$ phase shift, which is less than $2\pi$. Thus, the integer "n" may take on different values (e.g. 0, 1, 2, 3, ...) and, specifically, for the light beam 22b (FIG. 2A) n=0, while for the light beam 22c (FIG. 2B) n=1. In all cases, the total phase shift 36 for each light beam 22 is determined by comparing it with the corresponding light beam 22 in a plane wavefront. The total modular phase shift 38 can then be subtracted from the total phase shift 36 to obtain the individual phase shift 40 for the particular light beam 22. First, however, the total phase shift 36 should be determined.

Figure 3:
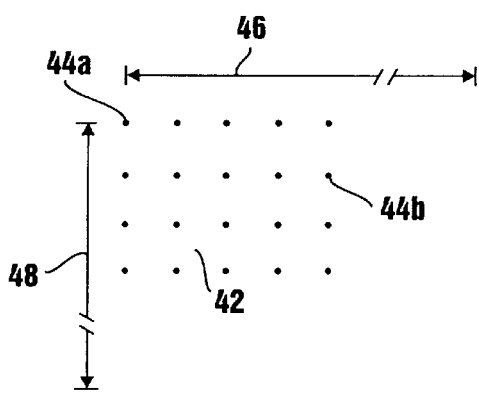
FIG. 3 is a plan view of a portion of a sensor array, including a plurality of sensor reference points.

A sensor array 42 is shown in FIG. 3 which can be incorporated into the wavefront sensor 14 to determine the total phase shifts 36 of each individual light beams 22 in a distorted wavefront 20. Specifically, as typically used for a Hartmann-Shack type sensor, the sensor array 42 includes a plurality of reference points 44, of which the reference points 44a and 44b are exemplary. As shown, these reference points 44 are arranged in columns and rows which have a length 46 and a width 48. In a manner known in the pertinent art, when a plane wavefront 24 is detected, each of the individual light beams 22 in the plane wavefront 24 will be directly incident on a respective reference point 44. For a distorted wavefront 20, however, the respective light beams 22 will be diverted from the respective reference point 44.

It happens that for each light beam 22 the magnitude of this diversion from the reference point 44 is proportional to the phase shift between the light beam 22 and its corresponding light beam in a plane wavefront 24. Thus, the total phase deviation 36 of a light beam 22 can be measured relative to a reference point 44 in the wavefront sensor 14.

Figure 4A:
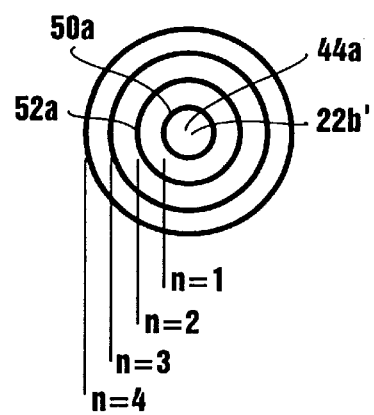
FIG. 4A is a single sensor reference point in the sensor array shown in FIG. 3 detecting a phase shift of less than $2\pi$.
Figure 4B:
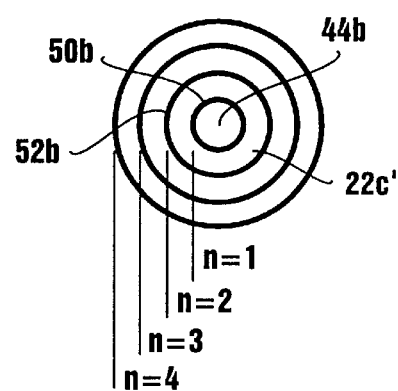
FIG. 4B is a single sensor reference point in the sensor array shown in FIG. 3 detecting a phase shift of more than $2\pi$.

In FIG. 4A, the sensor reference point 44a is considered by way of example. By cross referencing FIG. 2A with FIG. 4A, it is to be appreciated that the light beam 22a, which is exemplary of a light beam 22 in a plane wavefront 24, will be directly incident on the reference point 44a. On the other hand, a light beam 22 having a modular phase shift 38 of $2\pi$ (i.e. n=1), with a zero individual phase shift 40, will be incident on the ring 50a. Similarly, a light beam 22 having a modular phase shift 38 of $4\pi$ (i.e. n=2), with a zero individual phase shift 40, would be incident on the ring 52a, and so on. Now, while still cross referencing FIG. 2A and FIG. 4A, specifically consider the light beam 22b which is incident on the sensor array 42 at the point 22b'. Because the light beam 22b has no modular phase shift 38 (i.e. n=0), but because it does have an individual phase shift 26, the light beam 22b is incident on the sensor array 42 within the ring 50 and near, but not on, the reference point 44a (see FIG. 4A). Next, while cross referencing FIG. 2B, FIG. 3 and FIG. 4B, consider the light beam 22c relative to the reference point 44b. Because the light beam 22c has a modular phase shift 38 which is equal to $2\pi$, as well as an individual phase shift 40, the light beam 22c will be incident on the sensor array 42 at the point 22c' which is near reference point 44b but between the ring 50 and the ring 52. In both of these examples, the computer 18 is able to account for the respective modular phase shifts 38 and consequently determine an individual phase shift 40 for each of the light beam 22b and 22c. A similar analysis, of course, can be done for each light beam 22 in a distorted wavefront 20.

Figure 5:
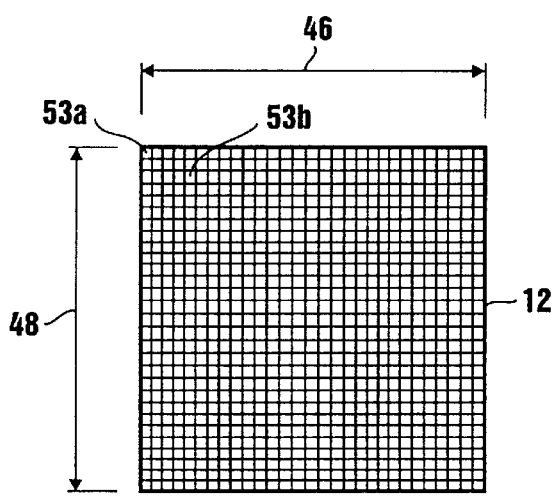
FIG. 5 is a plan view of the active mirror of the present invention as seen along the line 5—5 in FIG. 1.

Once a total phase shift 36 has been determined for each light beam 22, the modular ($n2\pi$) phase shift 38 can be easily accounted for. What is then left is the individual phase shift 40 ($<2\pi$) for each light beam 22. The individual phase shifts 40 are then converted by the computer 18 into signals that can be used to program the active mirror 12. Specifically, by cross referencing FIG. 3 with FIG. 5, it can be appreciated that for each reference point 44 in the sensor array 42, there is a corresponding subarray 53 of approximately two hundred facets 54 in the active mirror 12. For example, reference point 44a corresponds to the subarray 53a of facets 54, while reference point 44b corresponds to the subarray 53b of facets 54. Due to this correspondence, the individual phase shift 40 of each light beam 22 can be associated with a particular subarray 53 of facets 54 of the active mirror 12. As will be appreciated by the skilled artisan, each light beam 22 includes a plurality of light beams and, therefore, the tilt of each light beam 22 must be mimicked by a plurality of facets 54. Specifically, for the present invention, this is accomplished by separate subarrays 53 of facets 54.

Figure 6A:
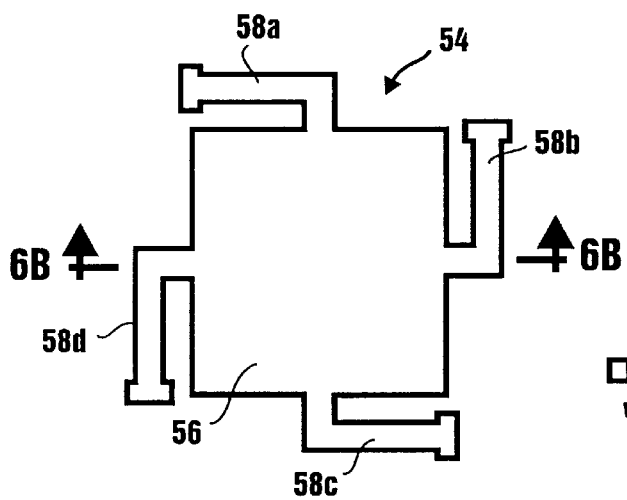
FIG. 6A is a plan view of an individual facet in the active mirror.

In FIG. 6A, a single facet 54 within each subarray 53 of the active mirror 12 is shown to have a reflective surface 56 which is supported by four extensions 58a–d. As indicated above, each facet 54 is dimensioned to be approximately a forty micron by forty micron square. Accordingly, when the active mirror 12 has a length 46 and a width 48, each equal to approximately eight millimeters, there will be two hundred facets 54 in each row along the length 46, and two hundred facets 54 in each column along the width 48. There are then a total of approximately forty thousand facets 54 in the active mirror 12.

Figure 6B:
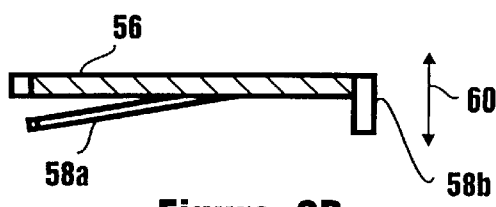
FIG. 6B is a cross sectional view of an individual fact in the active mirror as seen along a line 6B—6B in FIG. 6A.

As contemplated for the present invention, the extensions 58 for each facet 54 are responsive to signals from the computer 18 to move the reflective surface 56 back and forth along a path as indicated by the arrows 60 in FIG. 6B. More specifically, the distance of travel for the reflective surface 56 of each facet 54 in one direction is set to be approximately four tenths of a micron. Thus, a complete wavelength ($2\pi$), which is approximately eight tenths of a micron, can be accommodated by an individual facet 54. Consequently, each individual phase shift 40 ($<2\pi$) can be accommodated by an individual facet 54.

In one mode of operation for the system 10, a distorted wavefront 20 is directed by beam splitter 16 toward the wavefront sensor 14. Individual light beams 22 in the distorted wavefront 20 are then detected by the wavefront sensor 14, and the total phase shift 36 of each individual light beam 22, from a corresponding light beam 22 in a plane wavefront 24, is measured. Next, the computer 18 accounts for the modular phase shift 38 and, thus, determines an individual phase shift 40 for each individual light beam 22. These individual phase shifts 40 are then converted into signals that can be used to program the active mirror 12. Specifically, a signal that is proportional to the individual phase shift 40 of a particular individual light beam 22 activates a corresponding subarray 53 of facets 54 of the active mirror 12. The result of this activation are movements of the reflective surfaces 56 of respective facets 54 along a path in the direction of arrows 60 that is sufficient to compensate for the individual phase shift 40 of the light beam 22. This is done for each facet 54 in each subarray 53 of the active mirror 12. Consequently, when the distorted wavefront 20 is incident on the active mirror 12, the total phase shift 36 of each individual light beam 22 is compensated for, and the light in distorted wavefront 20 is reflected from the active mirror as a plane wavefront 24.

In another mode of operation for the system 10, it will be appreciated that a plane wavefront 24 can be converted into a predetermined distorted wavefront 20. This conversion can be accomplished simply by preprogramming the active mirror 12. Further, by using the wavefront sensor 14 and the computer 18 in a manner as described above, feedback control can be achieved to maintain the distorted wavefront 20.

While the particular Method for Programming an Active Mirror to Mimic a Wavefront as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for programming an active mirror to transform a plurality of contiguous light beams between a distorted wavefront and a plane wavefront, said active mirror having a plurality of individual facets with each facet being independently moveable along a respective substantially parallel path, wherein said method comprises the steps of:

positioning a plurality of individual facets of said active mirror to respectively reflect a wavefront comprising a plurality of contiguous light beams;

establishing a base datum for said facets, said base datum corresponding to a plane wavefront;

measuring an individual deviation in phase shift for each of said contiguous light beams in the wavefront relative to corresponding said light beams in a plane wavefront; and moving each said facet of said plurality of facets from said base datum through a distance on its respective path to minimize substantially all of said individual phase shift deviations, to transform the plurality of contiguous light beams between a distorted wavefront and a plane wavefront.

2. A method as recited in claim 1 wherein said plurality of individual facets establish a region and said active mirror includes at least one said region, and wherein said method further comprises the steps of:

identifying said region with an integer "n" wherein all of the light beams incident on said facets in said "n" region have a respective total phase shift, said total phase shift including said individual phase shift deviation and a same modular phase shift from said plane wavefront, said modular phase shift being equal to $n2\pi$; and compensating for said modular phase shift during said measuring step by subtracting $n2\pi$ from each said total phase shift to obtain said individual phase shift deviation.

3. A method as recited in claim 2 further comprising the steps of:

detecting boundary facets in said region wherein all said boundary facets have an $(n+1)2\pi$ modular phase shift with a zero individual phase shift deviation;

identifying an "n+1" region adjacent said boundary facets and outside said "n" region wherein all of the light beams incident on said facets in said "n+1" region have a respective total phase shift, said total phase shift including said individual phase shift deviation and a same modular phase shift from said plane wavefront, said modular phase shift being equal to $(n+1)2\pi$; and compensating for said modular phase shift during said measuring step by subtracting $(n+1)2\pi$ from each said total phase shift to obtain said individual phase shift deviation.

4. A method as recited in claim 2 further comprising the steps of:

detecting boundary facets in said region wherein all said boundary facets have an $(n-1)2\pi$ modular phase shift with a zero individual phase shift deviation;

identifying an "n-1" region adjacent said boundary facets and outside said "n" region wherein all of the light beams incident on said facets in said "n-1" region have a respective total phase shift, said total phase shift including said individual phase shift deviation and a same modular phase shift from said plane wavefront, said modular phase shift being equal to $(n-1)2\pi$; and compensating for said modular phase shift during said measuring step by subtracting $(n-1)2\pi$ from each said total phase shift to obtain said individual phase shift deviation.

5. A method as recited in claim 1 wherein said active mirror comprises an array of approximately forty thousand facets.

6. A method as recited in claim 1 wherein each said facet in said active mirror is substantially square and is approximately forty microns by forty microns.

7. A method as recited in claim 1 wherein each said facet moves along a respective said path through a distance of approximately four tenths of a micron.

8. A method as recited in claim 1 wherein said measuring step is accomplished using a Hartmann-Shack sensor.

9. A method as recited in claim 1 wherein said measuring step includes the step of determining an r.m.s. value for said deviation and said moving step involves minimizing said r.m.s. value of said deviation.

10. A method for transforming between a distorted wavefront and a plane wavefront which comprises the steps of:

dividing said distorted wavefront of light into a plurality of contiguous individual light beams;

comparing said distorted wavefront of contiguous individual light beams with a plane wavefront to determine a total phase shift deviation from said plane wavefront for each said individual light beams, said total phase shift deviation for each said individual light beam including an individual phase shift and an n2π modular phase shift, where "n" is an integer; and separately reflecting each said individual light beam to compensate for said total phase shift for transformation between said distorted wavefront and said plane wavefront.

11. A method as recited in claim 10 wherein said reflecting step further comprises the steps of:

providing an active mirror having a plurality of individual facets with each facet being independently moveable along a respective substantially parallel path;

positioning a plurality of individual facets of said active mirror to respectively reflect one said contiguous light beam; and moving each said facet of said plurality of facets through a distance on its respective path to minimize substantially all of said individual phase shift deviations.

12. A method as recited in claim 11 wherein a plurality of said individual facets establish a region, and wherein said method further comprises the steps of:

identifying said region with said integer "n" wherein all of the contiguous light beams incident on said facets in said "n" region have a same modular phase shift from said plane wavefront, said modular phase shift being equal to n2π; and compensating for said modular phase shift during said reflecting step by subtracting n2π from each said total phase shift to obtain said individual phase shift deviations for respective said individual contiguous light beams.

13. A method as recited in claim 12 further comprising the steps of:

detecting boundary facets in said region wherein all said boundary facets have an (n+1)2π modular phase shift with a zero individual phase shift deviation;

identifying an "n+1" region adjacent said boundary facets and outside said "n" region wherein all of the light beams incident on said facets in said "n+1" region have a respective total phase shift, said total phase shift including said individual phase shift deviation and a same modular phase shift from said plane wavefront, said modular phase shift being equal to (n+1)2π; and compensating for said modular phase shift during said measuring step by subtracting (n+1)2π from each said total phase shift to obtain said individual phase shift deviation.

14. A method as recited in claim 12 further comprising the steps of:

detecting boundary facets in said region wherein all said boundary facets have an (n−1)2π modular phase shift with a zero individual phase shift deviation;

identifying an "n−1" region adjacent said boundary facets and outside said "n" region wherein all of the light beams incident on said facets in said "n−1" region have a respective total phase shift, said total phase shift including said individual phase shift deviation and a same modular phase shift from said plane wavefront, said modular phase shift being equal to (n−1)2π; and compensating for said modular phase shift during said measuring step by subtracting (n−1)2π from each said total phase shift to obtain said individual phase shift deviation.

15. A device for transforming a wavefront between a distorted wavefront and a plane wavefront which comprises the steps of:

means for dividing said distorted wavefront of light into a plurality of contiguous individual light beams;

means for comparing said distorted wavefront of contiguous individual light beams with a plane wavefront to determine a total phase shift deviation from said plane wavefront for each said individual light beams, said total phase shift deviation for each said individual light beam including an individual phase shift and an n2π modular phase shift, where "n" is an integer; and means for separately reflecting each said individual light beam to compensate for said total phase shift for transformation between said distorted wavefront and said plane wavefront.

16. A device as recited in claim 15 wherein said comparing means is a Hartmann-Shack sensor.

17. A device as recited in claim 16 wherein said means for reflecting individual light beams is an active mirror having a plurality of individual facets with each facet being independently moveable along a respective substantially parallel path.

18. A device as recited in claim 17 wherein said active mirror comprises an array of approximately forty thousand said facets.

19. A device as recited in claim 17 wherein each said facet in said active mirror is substantially square and is approximately forty microns by forty microns.

20. A device as recited in claim 17 wherein each said facet moves along a respective said path through a distance of approximately four tenths of a micron.

* * * * *